United States Patent [19]
Deluca-Flaherty et al.

[11] Patent Number: 5,629,469
[45] Date of Patent: May 13, 1997

[54] THIOL PROTEASE INHIBITOR

[75] Inventors: Camille Deluca-Flaherty, Palo Alto; Victor J. Chan, Oakland; Liliana E. C. Scarafia, Mountain View; Karen J. Brunke, Belmont, all of Calif.

[73] Assignee: Sandoz Ltd., Basel, Switzerland

[21] Appl. No.: 384,367

[22] Filed: Feb. 10, 1995

Related U.S. Application Data

[63] Continuation-in-part of Ser. No. 208,571, Mar. 10, 1994.

[51] Int. Cl.$^6$ .......................... C12N 15/09; C12N 15/15; C12N 15/63; C12P 1/04; A01H 1/00; A01H 5/00
[52] U.S. Cl. .......................... 800/205; 47/58; 47/DIG. 11; 435/69.2; 435/71.1; 435/172.3; 536/23.5; 935/11; 935/23
[58] Field of Search .......................... 800/200, 205, 800/250, DIG. 56; 435/172.1, 172.3, 240.4, 240.48, 240.49, 240.5, 252.3, 252.33, 320.1, 69.2, 71.1; 536/22.1, 23.1, 23.2, 23.5; 47/58, DIG. 11; 935/11, 23

[56] References Cited

U.S. PATENT DOCUMENTS 5,196,304  3/1993  Kanost et al. .......................... 435/6

FOREIGN PATENT DOCUMENTS

| | | | |
|---|---|---|---|
| 0348348 | 6/1989 | European Pat. Off. | A01N 65/00 |
| 5238913 | 9/1993 | Japan | A01N 65/00 |
| 9221753 | 12/1992 | WIPO | C12N 15/11 |
| 9402504 | 2/1994 | WIPO | C07K 7/00 |

OTHER PUBLICATIONS

Laycock et al. "Molecular cloning of three cDNAs that encode cysteine proteinases in the digestive . . ." FEBS Letters, Amsterdam NL, v 292, pp. 115–120, Nov. 1991.
Laycock et al. "Molecular cloning of three cDNAs that encode cysteine proteinases . . ." FEBS Letters, Amsterdam NL, v 301, No. 1, p. 125, Apr. 1992.
Denizot et al "Novel structures of CTLA–2alpha and CTLA–2Beta expressed in mouse . . ." Eur. J. Immunol., v 19, pp. 631–635, 1989.
Masoud et al. "Expression of a cysteine proteinase inhibitor (oryzacystatin–I) in transgenic tobacco plants" Plant Mol. Biol., v 21, pp. 655–663, 1993.
Chen et al. "Rice cystatin: bacterial expression, purificiation, cysteine proteinase . . ." Protein Expression and Purification, v 3, pp. 41–49, 1992.
Guegler et al. "Cloning and characterization of thiol proteases from the False Colorado Potato Beetle" J. Cell. Biochem. Suppl., 18D, p. 134, 1994.
Ryan "Proteinase inhibitor gene families: Strategies for transformation to improve plant defenses against Herbivoris" Bioessays, v 10, 1, pp. 20–24, Jan. 1989.
Ryan "Proteinase inhibitors in plants: Genes for improving defenses against insects and pathogens" Ann.Rev.Phytopathol. v 28, No. 9, pp. 425–449, 1990.
Thomas et al. "Insect proteinase inhibitor expression in transgenic tobacco . . ." VIIth Inter. Congress on Plant Tissue and Cell Culture, Jun. 24–29 1990 p. 78.
Gillikin et al "Partial characterization of digestive tract proteinases . . ." Arch Insect Biochem Physiol, v 19 (4), pp. 285–298, 1992.
Johnson et al. 1989. Proc. Natl. Acad. Sci. USA. 86:9871–9875.
Brunke et al. 1991. TIBTECH. 9:197–200.
Hilder et al. 1987. Nature. 330:160–163.
Murdock et al. 1987. Comp. Biochem. Physiol. 87B:783–787.

*Primary Examiner*—Erich E. Veitenheimer
*Attorney, Agent, or Firm*—Lynn Marcus-Wyner

[57] ABSTRACT

A novel thiol protease inhibitor peptide is isolated from *Diabrotica virgifera* designated virgiferin. The DNA encoding virgiferin and modified virgiferin peptides are claimed. These sequences maybe cloned into vectors and used to transform plants conferring reduced susceptibility to damage by plant pests that have thiol proteases as digestive enzymes including insects and nematodes and particularly Coleopteran insects.

22 Claims, 6 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
      ( A ) LENGTH: 364 base pairs
      ( B ) TYPE: nucleic acid
      ( C ) STRANDEDNESS: single
      ( D ) TOPOLOGY: linear ( i x ) FEATURE:
      ( A ) NAME/KEY: CDS
      ( B ) LOCATION: 63..364

( i x ) FEATURE:
      ( A ) NAME/KEY: mat_peptide
      ( B ) LOCATION: 114..364

( x i ) SEQUENCE DESCRIPTION: SEQ ID NO:1:

```
CATCAGTTAA TCAACTGAAT TACTTGGTTA ATAAACTTCC AGTTCCTCTT CCACAATCAA        60

AA ATG TTT TGT AAA GTA TTT GTA CTT GCT CTC ATT GTA GCT GTT GCT          107
   Met Phe Cys Lys Val Phe Val Leu Ala Leu Ile Val Ala Val Ala
   -17     -15             -10                 -5

GTT GCA TCA CAA ACT GCT GAA GAA GCA TGG CCA AAA TAC AAG ACT GAT         155
Val Ala Ser Gln Thr Ala Glu Glu Ala Trp Pro Lys Tyr Lys Thr Asp
        1           5                   10

TAC AAT AGG AAC TAC GAC GCT CAG GAA GAT GCT ACA AGA TTC GCC ATT         203
Tyr Asn Arg Asn Tyr Asp Ala Gln Glu Asp Ala Thr Arg Phe Ala Ile
15              20                  25                  30

TTC AAG ACT AAC TAC GAC CAG ATC GAA GCA CAC AAC AAA AAG TTC GAA         251
Phe Lys Thr Asn Tyr Asp Gln Ile Glu Ala His Asn Lys Lys Phe Glu
                35                  40                  45

GCT GGT GAA GTA ACA TGG TCC ATG GGA TTG AAC CAA TTC GCT GAC AGG         299
Ala Gly Glu Val Thr Trp Ser Met Gly Leu Asn Gln Phe Ala Asp Arg
            50                  55                  60

ACC TTA GAA GAA CTA AAA CAT CTT CAT GGA GTT AGA CCT CCA GTA GGT         347
Thr Leu Glu Glu Leu Lys His Leu His Gly Val Arg Pro Pro Val Gly
        65                  70                  75

GCT ACT GGA GTA CAT  TA                                                  364
Ala Thr Gly Val His
80
```

( 2 ) INFORMATION FOR SEQ ID NO:2:

( i ) SEQUENCE CHARACTERISTICS:
        ( A ) LENGTH: 100 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Phe Cys Lys Val Phe Val Leu Ala Leu Ile Val Ala Val Ala Val
-17     -15             -10                 -5

Ala Ser Gln Thr Ala Glu Glu Ala Trp Pro Lys Tyr Lys Thr Asp Tyr
        1           5                   10                  15

Asn Arg Asn Tyr Asp Ala Gln Glu Asp Ala Thr Arg Phe Ala Ile Phe
                20                  25                  30

Lys Thr Asn Tyr Asp Gln Ile Glu Ala His Asn Lys Lys Phe Glu Ala
            35                  40                  45

Gly Glu Val Thr Trp Ser Met Gly Leu Asn Gln Phe Ala Asp Arg Thr
        50                  55                  60

Leu Glu Glu Leu Lys His Leu His Gly Val Arg Pro Pro Val Gly Ala
    65                  70                  75

Thr Gly Val His
80
```

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Ser Gln Thr Ala Glu Glu Ala Gly Pro Lys Tyr Lys Thr Asp Tyr Asn
1           5                   10                  15
```

Ala ( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GARGARGCNG RNCCNAARTA WAARAC                                                        26

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

AACTGGAAGA ATTCGCGGCC GCAGGAA                                                  27

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CTGAATTTGT GAACCCAA                                                                       18

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GAATTGAAAG CAAATATCAT GCG                                                            23

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CATGGACCAT GTTACTTCAC CAGCTTCG                                                28

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GTTGTGTGCT TCGATCTGGT CG                                                             22

( 2 ) INFORMATION FOR SEQ ID NO:10:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GCGCGTCGAC  CATGGCGAAT  TCACAAACTG  CTGAAGAAGC                    40
```

( 2 ) INFORMATION FOR SEQ ID NO:11:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
CCGGCTGCAG  AAGCTTTTAA  TGTACTCCAG  TAGCACC                       37
```

THIOL PROTEASE INHIBITOR

This is a continuation-in-part of Ser. No. 08/208,571, filed Mar. 10, 1994.

This invention is concerned with novel protease inhibitor peptides, nucleic acid sequences encoding these peptides, incorporation of protease inhibitor genes into the genome of a plant and the expression of the inhibitor gene or genes in plants wherein said plants have reduced susceptibility to damage caused by plant pests including insects and nematodes. The invention is further directed to biotechnological methods for producing said inhibitor peptides, insecticidal compositions containing said inhibitor peptides and the use of said peptides in combatting or reducing insect damage to plants.

BACKGROUND OF THE INVENTION

Certain plant pests particularly Colepteran insects and those insects of the genus Diabrotica cause tremendous damage to crop plants. In the past and currently, chemical fumigation has been used to control such insect damage. Additionally crop rotation practices can control Diabrotica populations. However, excessive use of insecticidal chemicals is not environmentally desirable and the practice of crop rotation may not be feasible for all growers. There is also increasing evidence that annual crop rotation may not provide complete protection from Diabrotica due to the increased prevalence of extended diapause in some Diabrotica populations. Therefore a means of protecting the plants from such insect damage by a mechanism other than chemical control or crop rotation would be very beneficial.

Proteases or peptidases, hereinafter referred to collectively as proteases, are enzymes which hydrolyze peptide bonds in proteins or peptides and demonstrate this activity at the ends of peptides (exopeptidases) or within the peptide chain (endopeptidases). The endopeptidases in particular cleave internal peptide bonds with different degrees of specificity for particular amino acyl residues. The protease enzymes are classified on the basis of their catalytic residues. Thus, with thiol proteases a cysteine sulfhydryl group participates directly in cleavage of the substrate peptide bond. Proteases are ubiquitous in nature and it is well documented that these enzymes are present in insect and other plant pests.

Peptides are generated from proteins in the gastrointestinal tract of organisms by the action of proteases during digestion. These organisms must rely on the activity of a battery of potent gut proteases in order to obtain all amino acids. The best characterized insect proteases are serine proteases (Applebaum, S. W. (1985) Biochemistry of Digestion, in Comprehensive Insect Physiology. Biochemistry and Pharmacology, Kerkut, G. A. and Gilbert, L. eds. 4:279–311. Pergamon Press, Oxford). In contrast, less polyphagous insects may employ acid proteases (Pendola, S. and B. Greenburg, (1975) Ann. Ent. Soc. Am. 69:341–345) or thiol proteases (Murdock et at, (1987), Comp. Biochem. Physiol. 87B:783–787) as major contributors in protein digestion. The gut of *Diabrotica virgifera*, common name, western corn rootworm (wCRW) has been found to be particularly rich in thiol proteases (Murdock et al, supra).

Molecules which form complexes with proteases and inhibit their proteolytic activity are also widespread in nature and they are regulators of proteolytic activity. The presence of a peptide inhibitor of thiol proteases, known as cystatin, was first described in 1957. Since this initial discovery, many cystatin type inhibitors have been characterized, and these inhibitors are generally referred to as members of the cystatin superfamily. The three subgroups of the superfamily include: the cystatins, containing disulfide bond(s); the stefins, lacking cysteine residues; and the kininogens which are high molecular weight glycoproteins with disulfide bonds.

Protease inhibitors are among the defensive chemicals in plant tissue that are both developmentally regulated and induced in response to insect and/or pathogen attack. Suppression of serine protease inhibitor expression in transgenic tomato plants has been demonstrated to result in reduced tolerance to insect feeding.

Certain thiol protease inhibitors that are toxic to insects and in particular Coleoptera are well characterized. In three species of beetles studied by Murdock et al, (supra) it was found that much or most of the proteolytic activity in the midgut extracts was inhibited by E-64, [N-(L-3 transcarrboxyoxiran-2-carbonyl)-L-leucyl]-amido(4-guanido)-butane, a specific, potent nonprotein inhibitor of thiol proteases.

The present invention is particularly concerned with the discovery of a novel peptide designated virgiferin as an effective thiol protease inhibitor. The amino acid sequence of virgiferin and modified virgiferin distinguishes these peptides from thiol protease inhibitor members of the cystatin superfamily.

SUMMARY OF THE INVENTION

In accordance with the invention a thiol protease inhibitor, hereinafter referred to as virgiferin is provided which is about a 11.5 kDa peptide with an amino acid sequence beginning at amino acid position 1 and ending at amino acid position 83 of SEQ ID NO.: 1 and SEQ ID NO.: 2. Virgiferin is believed to be a novel and unique peptide. No peptide with the foregoing amino acid sequence and combination of properties is believed to have been described heretofore. SEQ ID NOS.: 1 and 2 also provide the amino acid sequence for the signal peptide extending from amino acid position −17 to position −1.

In accordance with another aspect of the invention are modified virgiferin peptides, said modified peptides are functionally equivalent to virgiferin and comprise peptides having substantial amino acid sequence similarity to virgiferin; truncations of virgiferin; and truncations of peptides having substantial amino acid sequence similarity to virgiferin.

In accordance with still another aspect of this invention are recombinant nucleic acid sequences which encode virgiferin, or modified virgiferin (defined hereinbelow). Further DNA constructs are provided comprising a promotor which functions in a host cell and a DNA sequence encoding one or more of said virgiferin peptides.

Also embodied by the invention is a method for controlling insect or nematode infestation which comprises producing genetically transformed plants which have decreased susceptibility to damage by insect or nematode pests comprising inserting into the genome of a plant cell a DNA construct of the invention, obtaining transformed plant cells and regenerating from the plant cells genetically transformed plants which have reduced susceptibility to damage by insect and nematode pests and particularly to damage by Coleoptera.

This method for controlling insect or nematode infestation may also include providing plant-colonizing microorganisms which have been transformed to express a gene for virgiferin or modified virgiferin and wherein said microorganisms are introduced to a plant or plant loci where control is desired and wherein said gene is expressed in an insecticidally or nematodicidally effective amount.

The invention also envisages propagating or regenerating a genetically transformed plant as defined above and using plant cells, tissue cuttings, or seed to produce progeny that also display reduced susceptibility to damage by insect pests and in particular to Coleopteran insects such as Diabrotica. The invention additionally covers the progeny produced by said propagation or regeneration.

Another embodiment of the invention includes the production of protein derived from the expression of virgiferin and modified virgiferin in host microbial cells, and in particular including E. coli and root-colonizing organisms.

Other objects and features of the invention will become apparent from the following detailed description. It should be understood that the detailed description and specific examples are by way of illustration only.

DETAILED DESCRIPTION OF THE INVENTION

Figure 1:
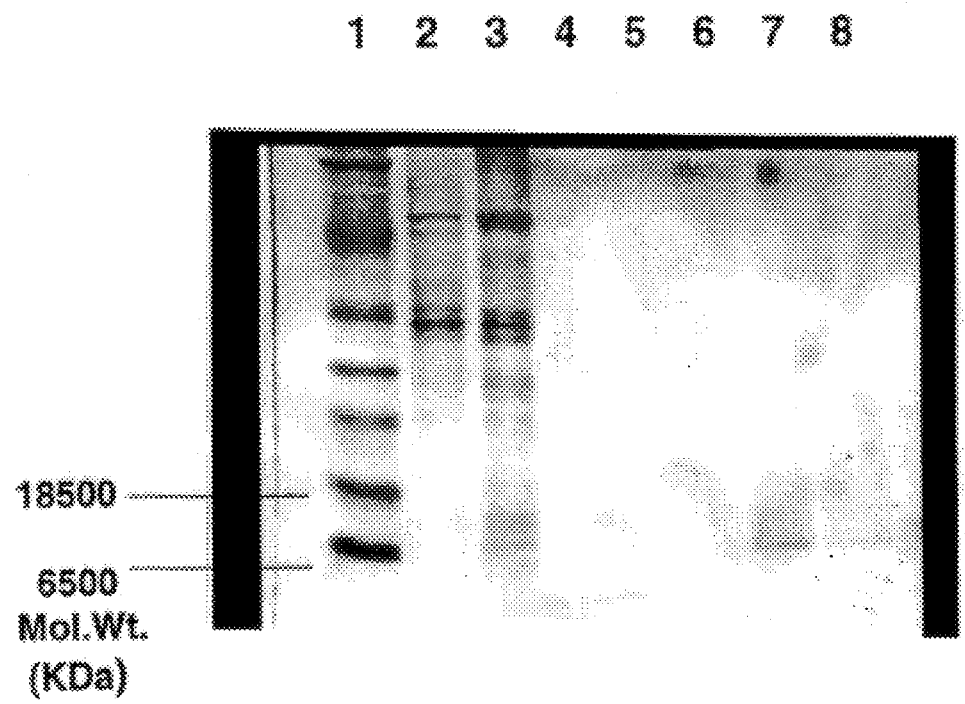
FIG. 1 describes the Laemmli gel of proteins extracted from wCRW pupae and subjected to cm-papain chromatography.

The novel thiol protease inhibitor, virgiferin, is defined by the amino acid sequence of SEQ ID NOS.: 1 and 2 starting at amino acid position 1 and ending at amino acid position 83. The position numbering is from the N-terminal serine (Ser) of virgiferin. Virgiferin is a potent inhibitor of Diabrotica digestive proteases. Pre-virgiferin is encoded as the precursor protein with a signal leader sequence of SEQ ID NOS.: 1 and 2 starting at amino acid position −17 to position −1. As used herein a "signal sequence" also referred to as a leader sequence is about 11 to about 22 amino acids. These amino acids are cleaved during maturation of the protease inhibitor. Leader sequences are well known in the an and are specific N-terminal sequences known to efficiently direct the mature peptide to the endoplasmic reticulum, vacuole or extracellular space via translocation through the endoplasmic reticulum membrane and which are excised during translocation. Examples of leader sequences include not only the PRMS (P14) sequence used in pZO1732 herein but also those from endoproteinase B gene and the tobacco PRIG gene among others. As used herein the term protease includes proteinases, and exo and endo-peptideases and means enzymes which hydrolyse peptide bonds in proteins and peptides. Further as used herein the term "protease inhibitor" refers to a molecule that reduces the level of proteolytic activity or esterase activity of a given protease enzyme.

The invention includes modified virgiferin peptides that may be isolated or constructed through standard techniques. Modified virgiferin peptides are functionally equivalent to virgiferin and have substantial amino acid sequence identity to virgiferin, or are truncations of virgiferin, or truncations of peptides with substantial amino acid sequence identity thereto. A functionally equivalent peptide is one wherein one or more amino acids have been added, substituted or removed without substantially reducing the peptides' protease inhibitory activity as compared to virgiferin. One skilled in the art is aware that various amino acids can be replaced or deleted in a peptide and yet that peptide still maintains its function. In this regard, a modified functionally equivalent peptide may include peptides with an even higher level of insecticidal or nematodical activity than virgiferin. Such modified peptides are preferred to have at least 50% identity or similarity to the amino acid sequence of virgiferin, preferably at least 70% similarity and more preferably at least 90%. For the purpose of the present invention, conservative replacements may be made between amino acids within the following groups: i) alanine, serine and threonine; ii) glutamic acid and aspartic acid; iii) arginine and lysine; iv) asparagine and glutamine; v) isoleucine, leucine, valine and metehionine; and vi) phenylalanine, tyrosine and tryptophan.

Modified virgiferin peptides and peptides of thiol proteases may be characterized by a molecular weight of about 10–15 kDa on an SDS PAGE with binding affinity to papain type proteases. Papain is well known to those skilled in the art as a thiol protease of defined three dimensional structure (Drenth, J et al., (1976) Biochemistry 15:3731–3738). A propeptide of a thiol protease is defined as the portion of the precursor thiol protease which is enzymatically cleaved from the catalytic protease peptide upon activation or maturation of the protease. In the case of papain type thiol proteases, propeptides occur amino-terminal to the enzymatic peptide. Additionally, modified virgiferin peptides may include peptides isolated from a Coleopteran insect and particularly a Diabrotica.

In this regard the invention also includes polymorphic clones of virgiferin. In particular at amino acid position 64 of SEQ ID NO.: 1, wherein proline or leucine may occur; and at amino acid position 73, where valine or leucine may occur. A summary of these polymorphisms is shown in Table 1.

The invention also includes peptides generated by truncation of virgiferin and virgiferin peptides modified either by genetic or chemical means while still maintaining the protease inhibitor function. Truncations refer to the elimination of amino acid sequences from the amino terminal and/or carboxy terminal ends of the peptide. Further the invention covers fusion proteins in which virgiferin sequences or modified virgiferin sequences are joined to the sequence of another protein or peptide either by chemical or genetic means. Fusion proteins may include either peptides joined in tandem or where the virgiferin sequence or modified virgiferin sequences are interrupted.

As noted one aspect of the invention is to produce virgiferin and modifications thereof through recombinant DNA techniques as well as to provide host cells that have been genetically transformed with nucleic acid sequences which code for virgiferin and modifications thereof. Host cells may include plant cells and bacterial cells.

DNA constructs suitable for transformation include at minimum the foreign gene including a promoter and coding sequence for virgiferin or modified virgiferin. The DNA sequences of the present invention can be obtained using various well known methods. The DNA may be synthesized by polymerase chain reaction, chemically synthesized or from isolation of double stranded DNA sequence from genomic DNA or complementary DNA (cDNA) which contains the sequence. The cDNA sequence of virgiferin is described in SEQ D No.: 1.

As is known in the art, the degeneracy of the genetic code allows for various nucleic acid sequences, DNA's and RNA's to encode the same protein, and in most cases an amino acid is encoded by two or more synonymous codons, for example the amino acid alanine is encoded by GCU, GCC and GCA. When cloning the peptides of the invention in another host organism, it may prove desirable to alter the nucleic acid codons such that those preferred by the host organism are employed, although no changes are made in the translation product. In this regard the invention also includes these synonymous codon sequences. The invention further includes not only preferential codon usage by a host organism but also changes in the polyadenylation sequence and intron slice consensus sequences.

The invention includes nucleic acid sequences which hybridize under stringent hybridization conditions with the cDNA virgiferin sequence or a portions thereof as disclosed herein. "Stringent hybridization conditions" are those in which hybridization is effected between 50° and 60° C. in saline buffer solution. The DNA to be used for hybridization may be prepared in a conventional manner and may be targeted to form an identifiable hybridization probe by procedures well known in the art. Such a probe may also be used to probe suitable and conventionally prepared clone banks to locate and isolate nucleotide alleles of virgiferin or to locate and isolate genes coding for virgiferin or modifications thereof in other Coleopteran insect pests. Particularly the nucleic acid segments or probes may be labeled chemically or radiochemically and used in Northern Hybridization, Southern Hybridization and colony or plaque hybridization to identify similar or identical segments from *Diabrotica spp.*

Vectors comprising the nucleic acid sequences described above represent another embodiment of the invention. Expression vectors are typically plasmids. Plasmids in general are circular double stranded DNA loops including a promotor operably linked to the DNA sequence or sequences encoding a protein of interest, transcription termination sequences and the remaining vector with 3' and 5' elements. One skilled in the art is aware of many types of vectors including virus vectors, baculovirus; phage vectors; Agrobacterium-Ti plasmid; binary vectors and other vectors suitable for plant transformation. The insertion of the DNA sequences into microbial and plant host cells according to the invention occurs according to techniques known in the art.

Promoters refer to nucleotide sequences at the 5'-end of a structural gene which direct the initiation of transcription and include all the regulatory regions required for transcription including the region coding for the leader sequence of mRNA. A number of promoters which are active in microbial and plant cells have been described in the literature. Suitable plant promoters include nopaline synthase (NOS), octopine synthase (OCS), cauliflower mosaic virus (CaMV) 19S and 35S, ribulose bisphosphate carboxylase (RUBISCO), and heat shock Brassica promotor (HSP 80). Suitable promoters used in the transformation of *E. coli* include, but are not limited to $P_{Tac}$, $\lambda_{pr}$ and $T_7$ which are available commercially. The promoters used in the present invention may be modified to affect control characteristics and further may be a composite of segments derived from more than one source, naturally occurring or synthetic. Termination sequences refer to a nucleotide sequence at the end of a transcriptional unit that signals termination of transcription. Terminators are 3'-non-translated DNA sequences that contain a polyadenylated signal Examples of terminators are known and described in the literature and include but are not limited to nos (nopaline synthase terminator), the 35S terminator of CaMV and the zein terminator.

Vectors of the invention may also include other DNA sequences known in the art, including but not limited to: a) stability sequences; b) one or more marker sequences, for example, antibiotic or herbicide resistance markers including cat (chloramphenicol acetyl transferase), npt II (neomycin phosphotransferase II), PAT (phosphinothricin acetyltransferase the expression of which confers resistance to the herbicide Basta); EPSPS (5-enolpymuvyl-shikimate 3-phosphate synthase, the enzyme inhibited by glyphosate, the active ingredient in the herbicide Roundup) and bxn (bromoxynil-specific nitrilase); c) other insecticidal protein genes such as delta endotoxin sequences for a *Bacillus thuringiensis;* d) intron sequences; and e) enhancer or other elements necessary to increase or decrease levels of expression obtained in particular parts of plants under certain conditions. These examples are stated by way of example only and are not intended to limit the invention in any manner.

A wide variety of techniques are available and known in the art for carrying out the actual transformation and transfection. These include but are not limited to, direct transfer of DNA into whole cells, tissues or protoplasts, optionally assisted by chemical or physical agents to increase cell permeability to DNA, for example, treatment with polyethylene glycol and dextran sulfate; electroporation, heat shock and ballistic implantation of DNA coated particles. Transformation is also mediated by Agrobacterium strains, notably *A, tumefaciens,* and also by various genetically engineered transformation plasmids which include portions of the T-DNA of the tumor inducing plasmids of Agrobacteria. Other means for effecting entry of DNA into cells include the use of viral vectors, agroinfection, binary vectors and cotransformation. (See Jensen et al., (1993), Techniques for Gene Transfer, pp 125–146 in Transgenic Plants, vol. 1, eds. King and Wu, Academic Press). Transformed or transfected bacterial cells are included in the present invention, for example *E. coli* and *Bacillus thuringiensis* (B.t.). Considerable experience in biotechnology has already been achieved and a wide variety of suitable operatively functional plasmids and transfer expression vectors systems are known and available for these organisms.

As used herein the term "genetic transformation" means the stable integration of a foreign gene into the genome of a plant regenerated from nucleic acid treated plant protoplasts, cells or tissue. "Transgenic plants" as used herein refers to plants carrying the stably integrated foreign gene. A "foreign gene" is a term used in the art to denote a gene or group of genes which has been transferred to a host cell or host plant from a source other than the host cell or host plant. The terms "transgene" or "exogenous gene" have the same meaning as the term foreign gene as used in this application.

Virtually all plants of agronomic or horticultural value are known to be both transformable and regenerable. The techniques vary in individual detail from species to species as is well recognized by one skilled in the art. Means of regenerating plants are well documented in the literature. For a review on plant transformation and regeneration, see Ritchie and Hodges, pps. 147–178, in Kung and Wu, Transgenic Plants, vol, 1, 1993, Academic Press. Plant tissue includes differentiated and undifferentiated tissue and cells of plants including but not limited to roots, shoots, leaves, pollen, embryos, seed and various forms of aggregations of plant cells including callus.

The present invention involves the preparation of recombinant DNA molecules that function in host cells and particularly in plant cells to produce decreased susceptibility to damage by plant insect pests and other plant pests that utilize cysteine digestive proteases. Such insect pests include in particular insects of the families Teuebdonidae, Curculionidae, Bruchidae and Chrysomelidae. Mention is made of insects of the genus Diabrotica. Exemplary of such plant insect pests are the species *adelpha, balteata, barbed, speciosa, undecimpunctata, howardi, virgifera,* and *viridula* commonly referred to as banded cucumber beetle, northern corn rootworm, spotted cucumber beetle, southern corn rootworm, western corn rootworm and Mexican corn rootworm. Other specific insects include Mexican bean beetle, Colorado potato beetle, wireworms, grubs, bollweevils, maize, grainery and rice weevils and Bruchids.

Decreased susceptibility to damage by plant pests may be provided by expressing one of the virgiferin peptides of the invention in a root-colonizing organism wherein the organism is applied to the plant or to a loci around the plant and as the pest feeds on the plant it ingests an insecticidally effective amount of the virgiferin peptide produced by the organism. Root-colonizing organisms may be bacterial or fungal and further may be surface colonizers or endophytes.

Plants which may be made less susceptible to damage by insect or nematode pests by the practice of the present invention include but are not limited to those plants that are members of Gramineae, Cucurbitaceae, Leguminoseae, Solanaceae, Compositeae, Cyperaceae, Convolulaceae. Specific mention is also made of the following plants: corn (maize), sweet corn, squash, melon, cucumber, sugarbeet, sunflower, rice, cotton, canola, sweet potatoes and legumes including peanuts, common bean, cowpea, soybean, alfalfa and broad bean.

One further aspect of this invention comprises an insecticidal composition comprising as its active ingredient an insecticidally effective amount of a peptide as claimed in the present invention and in particular virgiferin. The term "insecticidally effective amount" or "nematodical effective amount" means an amount sufficient to achieve control of an insect or nematode plant pest by reducing the number of insects or nematodes through mortality, reduced growth (stunting), reduced reproductive efficiency and the like. Virgiferin or a modification thereof may be formulated in a number of ways well known to those skilled in the art. Formulations used in spray form such as water dispersible concentrates or wettable powders, may contain surfactants such as wetting agents or dispersing agents. Further active ingredients, for example pesticides including fungicides, insecticides and herbicides may be applied together with the peptides of the invention in order to increase their spectrum of activity or agricultural utility. The formulations may be applied at a locus where control is desired. The amount of active ingredient will vary depending on many factors, including the nature of the particular formulation.

EXAMPLES

The following examples are provided to illustrate the invention and are not intended to limit the scope of the invention. The examples utilize many techniques well known in the field of molecular biology and particularly with respect to manipulation of recombinant DNA in plant tissue with the concomitant transformation of plant tissue. The techniques are described in further detail by the cited references which are hereby incorporated by reference.

Example 1: Isolation and Purification of Virgiferin from wCRW pupae.

Virgiferin is purified from homogenates of wCRW pupae based on cm-papain-agarose chromatography. (Barrett, A. J. (1981) Methods in Enzymology 80:771–778).

Preparation of cm-papain-agarose. Papain (Boehringer-Mannheim) is inactivated by carboxy-methylation as described in Barrett, supra, and then dialyzed overnight in 50 mM MOPS (pH 7.5) –10 mM iodoacetic acid. Cm-papain is coupled to Affi-Gel 15 agarose (BioRad) in 50 mM MOPS (pH 7.5) and washed successively with 50 ml PBS, 50 ml 50 mM sodium carbonate buffer (pH 10.5) and 50 ml PBS prior to storage in PBS containing sodium azide.

Pupae homogenate. Approximately 50 wCRW pupae (French Agricultural Research) are washed with PBS to remove field soil. The pupae are homogenized in 15 ml PBS and the homogenate is cleared of debris by centrifugation. The supernatant is heated to 56° C. for 5 minutes then centrifuged. The supernatant is mixed with 1.0 ml of cm-papain-agarose overnight at 4° C. The slurry is poured into a 10 ml disposable column and washed with PBS until detectable protein is not evident in the eluant The column is washed with 50 mM sodium carbonate buffer (pH 10.5). One ml fractions are collected and evaluated by visualization on Laemmli electrophoresis through 4–20% acrylamide gels for the presence of distinct peptides. A 11.5 kDa peptide is present as shown in FIG. 1 and the peptide is designated virgiferin.

Example 2: Determination of the virgiferin N-terminal amino acid sequence.

Cm-papain fractions containing relatively high concentrations of the virgiferin are pooled and lyophilized. Virgiferin is resolved from minor contaminants by SDS-PAGE as described previously. Using the method developed by Matsudaira (Matsudaira, P. (1987) J Biol Chem 262:10035–10038), virgiferin is electrophoretically transferred to a polyvinylidene diflouride membrane (Millipore) adjustments are made for transfer of low molecular weight proteins as follows. The acrylamide gel is soaked in transfer buffer (40% methanol, 10 mM TRIS (pH 8.8)) for one hour. Proteins are electrophoretically transferred overnight at 30 mA in transfer buffer to a PVDF membrane. An intense band of protein is visualized upon staining the membrane. The band is excised and subjected to automated protein sequence analysis. The sequence is determined by automated Edmund degradation and presented SEQ ID NO.: 3. In addition to the amino acid residues listed in SEQ ID NO.: 3, other residues are present in lesser amounts and these include in addition to Ser (amino acid residue 1), Asn and Ala; in addition to Gln (amino acid residue 2), Ile and Pro; in addition to Thr (amino acid residue 3), Ala and Leu; in addition to Glu (amino acid residue 5), Gly; in addition to Gly (amino acid residue 8) Asp; and in addition to Ala (amino acid residue 17), Arg.

Example 3: cDNA Synthesis and Cloning

PCR techniques are used to produce cDNA clones encoding virgiferin. Unless specified the starting templates for the PCR reactions are RNA purified from wCRW tissues as follows: RNA isolation and polyA+selection: Total RNA for PCR and Northern blot analysis is isolated from WCR third-instar gut and pupae. Tissue is homogenized in RNazol (Tel-Test) following supplier's protocol. PolyA+RNA is purified from total RNA by Poly(A)Quik oligo-dT cellulose (Stratagene).

Polymerase Chain Reactions: Polymerase chain reactions (PCR Protocols) are performed on a Peri-Elmer Cetus 9600 DNA Thermal Cycler. Reaction conditions are as follows: 2U Taq DNA polymerase (Pharmacia) in enzyme's buffer, 0.2 uM dNTP mix, 0.4 uM each of sense and antisense primer, and DNA template in water to a final volume of 50 μl. Template in water is denatured at 94 C./1 rain prior to the addition of the reaction mix at 82° C. The reaction cycle is 94 C./15 sec, 55 C./30 sec, 72 C./45 sec for 30 cycles, followed by a 72 C./3 rain extension.

Template DNA Synthesis: Template DNA for PCR is first-strand cDNA synthesized using the First-strand cDNA Synthesis Kit (Pharmacia). PolyA+ RNA (wCRW gut and pupal) are primed with the Not I-d(T)18 Bifunctional Primer from the kit. The sense primer for the initial PCR is a degenerate oligonucleotide, PKY: 5'GA(A/G)GA(A/G)GC(A/C/G/T)G(A/G)(A/C/G/T)CC(A/C/G/T)AA(A/G)TA(T/C) AA(A/G)AC3', SEQ. ID. NO.: 4, encoding the N-terminal amino acid sequence of the 11.5 kDa wCRW protein as determined above.

The antisense primer, TLESS: 5'AACTGGAAGAATTCGCGGCCGCAGGAA3', SEQ. ID. NO.: 5, is based on a portion of the Not I-d(T) 18 Bifunctional Primer.

A 600 base pair PCR product is obtained.

Purification and Cloning of PCR Products: PCR products are gel-purified in a 1.2% agarose gel in TBE. DNA is eluted from the excised gel fragment by electroelution. Gel-purified PCR products are ligated into the T-vector pT7Blue (R)(Novagen) using standard methods (Maniatis, supra).

Figure 4:
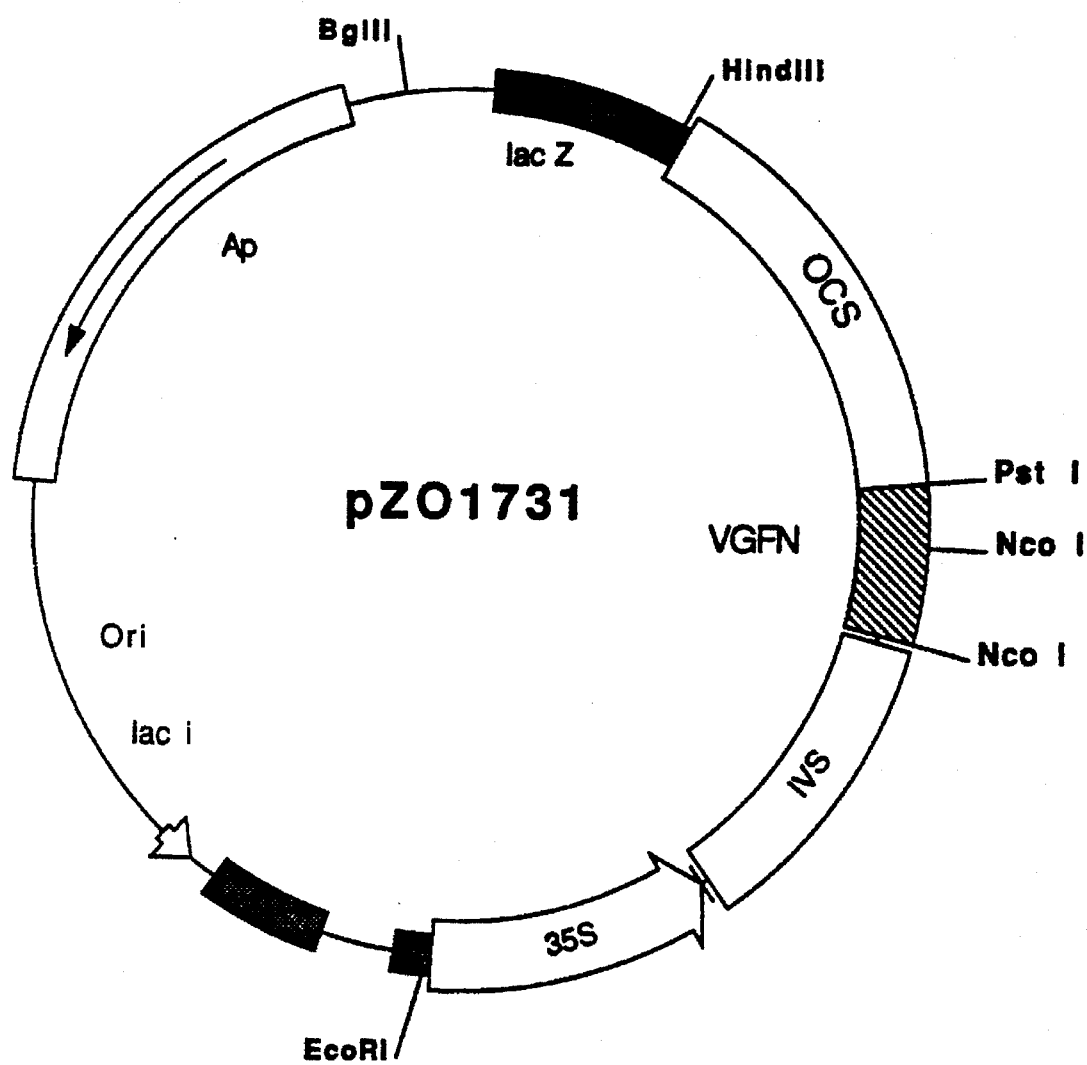
FIG. 4 describes a plasmid map of the plant expression construct pZO1731 encoding the virgiferin peptide.
Figure 5:
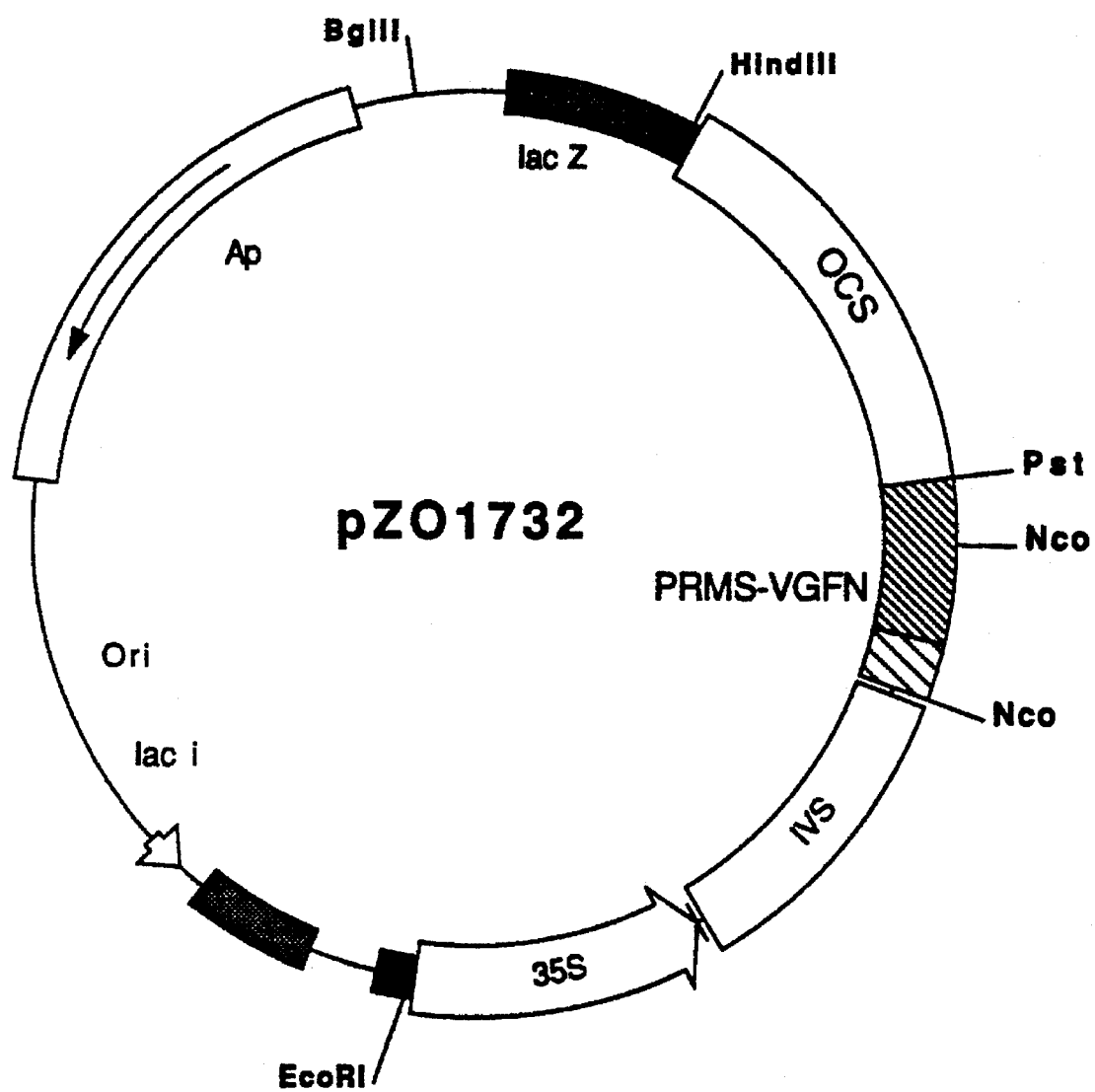
FIG. 5 describes a plasmid map of the plant expression construct pZO1732 encoding the virgiferin peptide which is fused to the PRMS (P14) leader peptide.

DNA Sequencing: Recombinant clones are selected using PCR techniques and cultured in 3 ml volumes. DNA is prepared from these cultures and are sequenced using standard methods. The sense primer for sequencing templates cloned in the plant expression vectors is IVS6END: 5'CTGAATTTGTGAACCCAA3', SEQ ID NO.: 6, based on the 3' end of intron 6, and the antisense primer is OCS rev: 5'GAATTGAAAGCAAATATCATGCG3', SEQ ID NO.: 7, based on the 5' end of the complete OCS terminator. These two primers flank the cloning sites of the plant expression vectors, pZO1731 and pZO1732 (FIG. 4 and 5 respectively). The construct pZO1732, DNA encoding the PRMS(P14) signal sequence is fused in frame with virgiferin as described by amino acid position 1 to 83 in SEQ ID NO.: 1. (Casacuberta, et al., (1991) Plant Mol. Biol. 16:527–536).

Cloning the 5'-end of the Virgiferin cDNA: Two nested antisense primers are designed for cloning the 5' end of the gene from the sequence data of the initial PCR-amplified DNA: VTW rev: 5'CATGGACCATGTTACTTCACCAGCTTCG3', SEQ. ID. NO.: 8 and DQ rev: 5'GTGGTGTGCTTCGATCTGGTCG3', SEQ. ID. NO.: 9. The 5' ends are cloned using the 5'RACE System (Cribco BRL) following manufacturer's protocol. The complete DNA sequence and deduced amino acid sequence of the propeptide (pre-virgiferin) is shown in SEQ ID NO.: 1 and includes the 17 amino acid leader peptide encoded in the 5'DNA.

Example 5. Expression of Virgiferin in *E. coli*

For construction of expression vectors, PCR primers are synthesized that introduce a methionine start codon and appropriate restriction sites. The sense primer SQT: 5'GCGCGTCGACCATGGCGAATTCACAAACTGCTGAAGAAGC3', SEQ. ID. No.: 10, introduces NcoI and EcoRI sites and the residues MAN just N-terminal to the first amino acid of the virgiferin peptide (starting at the Ser residue, amino acid position 1 in SEQ ID NO.: 1). The MAN residues represent the amino acids methionine, alanine and asparagine respectively. The antisense primer;

GVH rev: 5'CCGGCTGCAGAAGCTTTTAATGTACTCCAGTAGCACC3', SEQ. ID. NO.: 11) introduces HindIII and PstI sites after the stop codon. Both primers include four nucleotide "clamps" at their 5' end for facilitating restriction digests.

The DNA sequence encoding virgiferin is amplified using PCR technology from RNA isolated from wCRW gut as described previously, using the SQT and GVH rev primers. These primers introduce a methionine start codon and appropriate restriction sites. The resultant PCR products are purified and ligated into pT7Blue(R), screened and sequenced as before.

The DNA sequence reveals three polymorphisms in the population of clones: at amino acid position 64, proline or leucine; position 73, valine or leucine; and position 75, proline or arginine. For position 73 and 75, only one clone, V7-3, has leucine and arginine, respectively. The valine to leucine transition requires two base changes and the proline to leucine transition requires two base changes (CCA to TTA). Two polymorphic clones, V7-3 and V7-9 have been characterized and further developed in bacterial and plant expression constructs. A summary of these polymorphisms is shown in Table 1.

TABLE 1

| | Residue | | | Expression Vectors Based on Clone | |
|---|---|---|---|---|---|
| Clone | 64 | 73 | 75 | Bacterial | Plant |
| V7-3 | Pro | Leu | Arg | BN8 | VGP322(pZO1730) |
| V7-9 | Pro | Val | Pro | PEV4 | VNP31(pZO1731)<br>VRE92(pZO1732) |

The pT7Blue(R) construct encoding virgiferin with N-terminal MAN residues, described above, is digested with restriction enzymes EcoRI and HindIII. The DNA fragment encoding virgiferin is purified and ligated into the *E. coli* expression vector pET-20b(+)(Novagen), thus fusing the DNA sequence encoding MAN-virgiferin in frame with the DNA sequence encoding the *E. coli* pelB leader sequence. Transformed cultures are screened using PCR methods as described previously. DNA sequence analysis of PCR-positive clones confirmed in-frame fusions of the pelB leader with MAN-virgiferin. This construct is referred to as plasmid pEV4 and described in FIG. 3.

pEV4 is used to transform *E. coli* strain BL21(DE3). Freshly transformed colonies are transferred to liquid media and cultured as described Dubendorf, J. W. and Studier, F. W., (1991), J. Mol. Biol., 219:45–59 and Studier F. W. (1991) J. Mol. Biol. 219:37–44. Aliquots of the culture are removed at the time of induction and at intervals of 30 minutes, 60 minutes, two hours and four hours following induction and analyzed by SDS-PAGE. Abundant expression of a 10–12 kDa protein is apparent in samples taken two hours or later following induction.

Example 6. Purification of Recombinant Virgiferin.

For preparative purposes, 500 ml bacterial cultures are incubated 4 hours at 37 C. following induction for optimal yield. The cultures are harvested and hypotonically shocked to lyse the outer cell wall. See Lin, K. and Cheng, S. (1991) BioTechniques 11:748–752. The spheroplasts are separated from the periplasmic protein-enriched fraction by centrifugation. The periplasmic fraction contains nearly pure MAN-virgiferin which is stable at 4° C. for up to four weeks. In some cases this crude preparation of MAN-virgiferin is tested for proteolytic inhibitory activity.

For chromatographic purification of MAN-virgiferin 1M Tris-HCl (8.0) is added to the periplasmic fraction to make a final concentration of 50 mM Tris-HCl (8.0). The supernatant is applied to a DEAE Sepharose Fast Flow (Pharmacia) column in 50 mM Tris-HCl (8.0) at a flow rate of 3 ml/min. Proteins are eluted with a 0 mM–350 mM NaCl linear gradient in the same buffer. Column fractions are analyzed by SDS-PAGE. MAN-virgiferin is eluted from the DEAE column in a single peak at a relatively high NaCl concentration. The DEAE column fractions containing virgiferin are pooled and dialyzed in Spectrapor #1 (MW cutoff=6–8 kDa) tubing against 50 mM Phosphate, 150 mM NaCl (pH 7.0) for 2 hours. The protein is concentrated by ultrafiltration and applied to a Superose 12 (Pharmarcia) gel filtration column. The Superose column is developed with the 50 mM phosphate, 150 mM NaCl buffer at a flow rate of 0.3 ml/min. SDS-PAGE analysis of the Superose fractions verifies that MAN-virgiferin has been separated from a minor contaminant. The protein concentration of Superose fractions containing pure MAN-virgiferin is determined by Bradford assay and the fractions are tested directly for inhibitory activity against wCRW gut proteases.

Antibodies have been produced from the *E. Coli* virgiferin protein and have been shown to be of high quality and effective for Western blot analysis.

Example 7. Proteolytic Inhibition Activity of Virgiferin.

Midguts, free of fat bodies are dissected from wCRW third instar larvae (French Agricultural Research) by evisceration. The wCRW midgets are then suspended in 100 mM MES (pH 6.3) (1 gut/µl). Following a 60 minute incubation on ice, the tissue is pelleted by centrifugation (13 K rpm, 8 min) and the supernatant is collected for analysis. This fraction contains potent thiol protease activity(s) effective in a broad range of pH 5.0 to pH 8.0.

Figure 2:
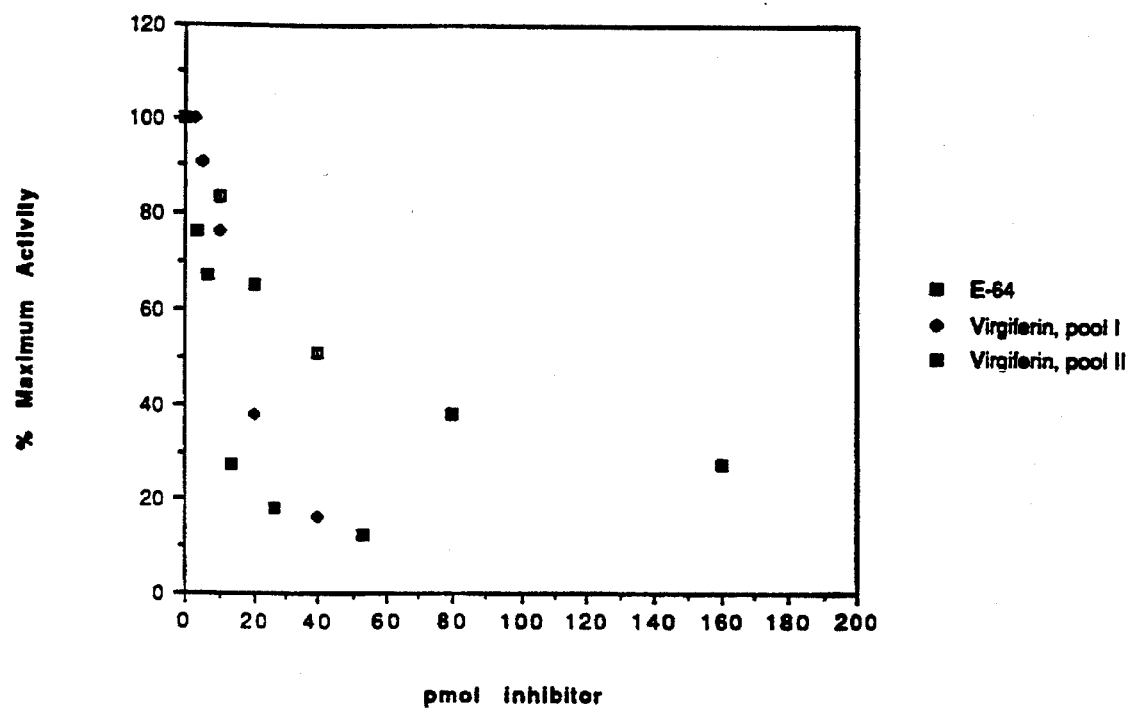
FIG. 2 describes an active site titration of wCRW gut proteases with the irreversible inhibitor E-64 and with two concentrations of MAN-virgiferin.
Figure 3:
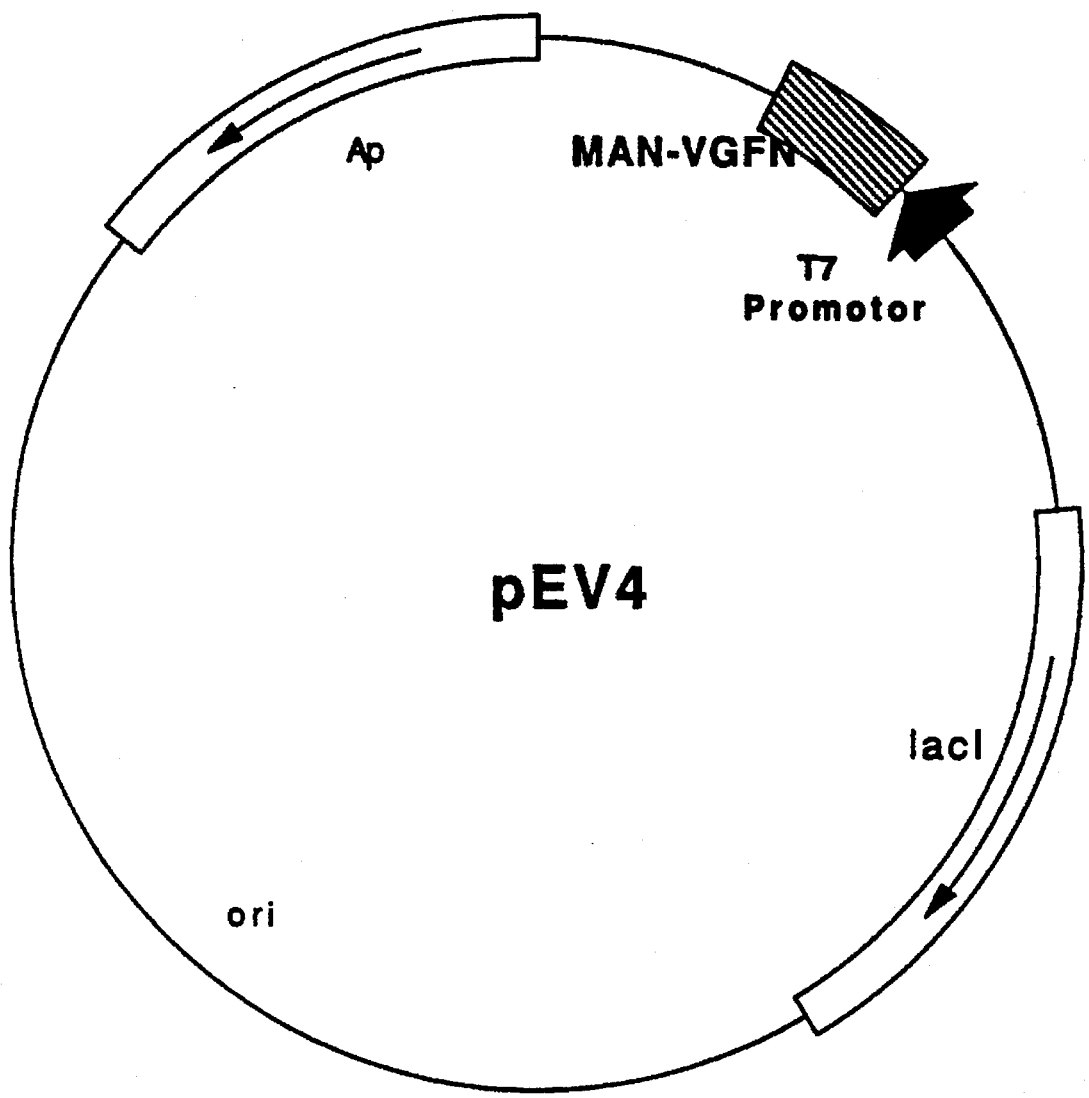
FIG. 3 describes a plasmid map of the E. coli. expression construct pEV4 encoding the virgiferin peptide.

Enzymatic activity of all preparations is measured against azocasein as described by Mason, R. W., Gal, S. and Gottsmart, M. M. (1987) Biochem J. 248:449–454. Active site titrations for all enzymatic preparations are performed using azocasein as the proteolytic substrate. All assays are performed at 37° C. for 60 minutes. The titration curves are normalized for full activity of each enzyme preparation in the absence of thiol protease inhibitors. Enzyme inhibition is reported as a proportion of full proteolytic activity under the same conditions in the presence of designated quantities of the irreversible thiol protease inhibitor E-64 or MAN-virgiferin. A typical active site titration of wCRW gut proteases is shown in FIG. 2. Repeatedly the titration curves obtained with MAN-virgiferin suggest potent inhibition of the wCRW gut proteases.

Example 8: Transformation and Regeneration of Maize Tissue

Corn ears, Hi Type II, 9 to 12 days after pollination are harvested for embryo isolation, sterilized and rinsed in sterile water. Embryos are excised aseptically from the kernels (Rhodes, C. A. et al., (1988) Bio/Tech. 6:56–60). Ten to 50 embryos are transferred to a solid N6ap1D medium, and stored in the dark at 27° C. for 0 to 5 days.

Embryos are transferred to petri dishes containing solid N6ap1D medium supplemented with 0.5M mannitol. Approximately 4 hours after transfer the embryos are subjected to particle bombardment DNA delivery or "shot" with the Biolistic PDS-1000/He Particle Delivery System using a standard Sanford protocol except that the ethanol (100%) is added to the particles so that the final volume of the suspension is 900 µL.

Figure 6:
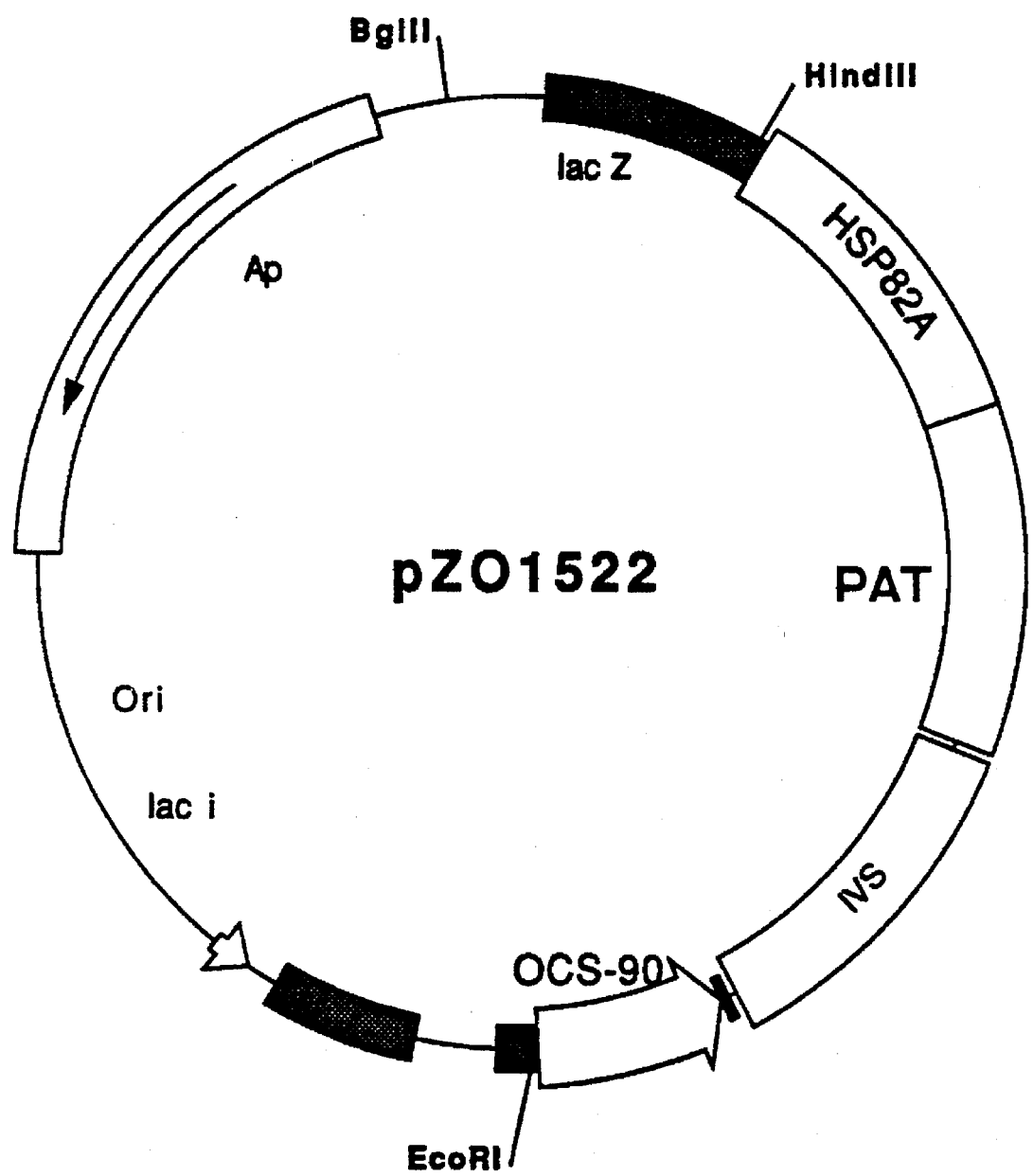
FIG. 6 describes a plasmid map of the plant expression construct pZO1522 which is delivered simultaneously with each virgiferin encoding construct.

The virgiferin encoding plasmids used in the transformation of maize tissue are described in FIGS. 4 and 5 and correspond to pZO1731 and pZO1732. pZO1731 includes the virgiferin encoding sequence, a 35s CaMV promoter, intron VI, and ocs termination sequences. pZO1732 includes the signal leader PRMS in addition to the sequence encoding virgiferin. Each virgiferin encoding plasmid is delivered simultaneously with plasmid pZO1522 depicted in FIG. 6. pZO1522 encodes the *Streptomyces hygroscopicus* phosphinothricin acetyltransferase (PAT) gene, the expression of which confers Basta resistance to transformed tissue. (Thompson C. J. et al., (1987) EMBO J. 6:2519–2523). Basta, common name glufosinate-ammonium, is a chemical herbicide containing phosphinothricin which inhibits glutamine synthase. The practice of co-shooting or mixing plasmid DNA's for particle delivery is known and described in the art (Gordon-Kamm et al., 1990, Plant Cell 2:603–681). The final volume of the suspension containing DNA-coated tungsten particles and ethanol is 900 µL prior to delivery to the embryos.

Following particle delivery the embryos are kept on N6ap1D medium supplemented with 0.5M mannitol for approximately 16 hours then transferred to fresh N6ap1D medium without selective agents for 0 to 5 days. Finally, the embryos are transferred to solid N61D medium supplemented with 13 to 24mg/L of Basta. Transfers are made to fresh selective media every 2 weeks or as needed.

Sixty days after transformation, callus and embryo tissue which continues to grow on N61D medium containing Basta are transferred to fresh medium containing 24 mg/L Basta. Samples of at least 50 ug of these transformant tissues are removed and analyzed for the presence of the DNA originally delivered by particle bombardment using PCR techniques.

To regenerate plants the callus is transferred to petri dishes containing solid MSap medium without growth hormones and stored in the dark at 27 C. for 15 days. Plant shoots formed under these conditions are transferred to fresh medium in boxes and stored at 27 C. under a cycle of 18 hours/24 hours of bright light. Ten days after transfer to boxes the developing plants that are greater than 3 inches in height and possess a root system are transferred to soil and stored in a growth chamber for 48 hours total. The relative humidity is adjusted to 50% and the plants maintained in a growth chamber for 1 to 2 weeks then transplanted into 5 gallon pots and maintained in a greenhouse with under a cycle of 18 hours/24 hours of bright light. Fertile, transformed plants are pollinated with control pollen and seed is collected.

Stability and segregation of the virgiferin gene is determined by analysis of germinated seedlings. Some of these results are indicated below. Each independently transformed line is shown to have the virgiferin gene by PCR analysis.

TABLE 2

|  | # of Stable Inherited Events | # of Events Showing Protein Expression |
|---|---|---|
| pZO1731 | 18 | 7 |
| pZO1732 | 15 | 3 |

Using the antibodies produced against the virgiferin protein in Example 5, transgenic plants are screened for the production of virgiferin. Protein expression is determined by Western blot analyses according to standard techniques (Antibodies, A Laboratory Manual, 1988, Ed. Harlow and David Lar, Cold Spring Harbor Laboratory). Western analyses also indicates that the protein is produced in both leaves and roots of transformed plants with both gene constructs.

Example 9: Insect Susceptibility Tests wCRW eggs (200–500) are disinfected and placed in a sterile environment to hatch. Larvae which hatch in 1 to 3 days are transferred to maize callus. Seven days following initial exposure of the larvae to the callus insecticidal activity is evaluated. The number of dead insects as well as the size of the surviving insects is recorded.

Example 10: Artificial Diet Bioassays

Neonate wCRW larvae are allowed to feed on BioServe, a standard artificial diet used for southern corn rootworm. The diet is supplemented with the treatments indicated below in Table 3. Two or 3 larvae are placed in treatment wells with 9 replicate wells used per treatment. The larvae are allowed to feed on the diet and mortality is evaluated at day 6. The results of the assay are given below.

TABLE 3

| Treatment | % wCRW mortality ± SE |
|---|---|
| virgiferin (4%)* | 100 ± 0 |
| E64 (0.01%) | 80 ± 8 |

TABLE 3-continued

| Treatment | % wCRW mortality ± SE |
|---|---|
| Standard Diet | 15 ± 8 |
| Standard Diet (10%) + Casein | 29 ± 15 |

*Virgiferin was obtained from the production of the protein in $E.\ Coli$. Estimated dose of virgiferin protein (w/v).

To confirm that the virgiferin effects are due to direct ingestion of the protein and not due to an antifeedant response. Food coloring, commercially available green dye, was added to the diet. Results indicate that the dye is readily taken up and is observed through the insects cuticle upon ingestion.

Example 11: Effect of Virgiferin against *Callosobruches maculatus* (cowpea weevil)

A dose response analysis of the effects of virgiferin was performed on *Callosobruchus maculatus*, the seed feeding cowpea weevil. Using an artificial seed bioassay system and an ultrasonic detector as disclosed in Shade, R. E. et al. (1986), Environ. Entomol. 15:1286–1291, disruption of the cowpea weevil's normal feeding pattern is determined by differences in mean feeding events. The results are indicated below in Table 4.

TABLE 4

Effect of virgiferin[a] on feeding activity of cowpea weevil

| Treatment | Dose % w/w[e] | Count[d] | Mean[b] Feeding Events | LSC[c] (0.05) |
|---|---|---|---|---|
| Virgiferin | 0.4 | 4 | 43 | a |
| Virgiferin | 0.2 | 5 | 70 | a,b |
| Virgiferin | 0.1 | 6 | 60 | a |
| Virgiferin | 0.05 | 5 | 61 | a |
| Virgiferin | 0.025 | 5 | 85 | a,b |
| Virgiferin | 0.031 | 5 | 107 | b |
| Control | 0.0 | 6 | 105 | b |

[a]Recombinant virgiferin is produced in $E.\ coli$ as described in Example 5.
[b]Mean number of feeding events detected in 30 sec samples.
[c]Fishers Protected LSD - means followed by the same letter are not significantly different.
[d]Count = Number of insects tested.
[e]Estimated dose of virgiferin protein in diet.

The results indicate that there was a reduction in the mean number of feeding events observed and this initial analysis suggests that virgiferin is active against cowpea weevil.

What is claimed is:

1. An isolated thiol protease inhibitor peptide designated Virgiferin having the amino acid sequence extending from amino acid position 1 to 83 of SEQ ID NO.: 1 and a modified virgiferin peptide wherein said modified peptide comprises a peptide having at least 50% amino acid identity to virgiferin; truncations of virgiferin; or a peptide having at least 50% amino acid identity to the truncations of virgiferin wherein said modified virgiferin is functionally equivalent to said virgiferin protease inhibitor.

2. An isolated pre-virgiferin peptide characterized by the entire amino acid sequence given in SEQ ID NO.: 1 and peptides having at least 50% amino acid sequence identity thereto.

3. A homogenous protease inhibitor peptide characterized by a molecular weight of about 10–15 Kda on an SDS PAGE with binding affinity to papain type proteases.

4. A recombinant DNA molecule comprising a nucleic acid sequence encoding the peptide according to claim 1.

5. A recombinant molecule according to claim 4 further comprising a signal leader sequence.

6. A recombinant molecule according to claim 4 characterized in that it is a vector.

7. Protein derived from the expression of the recombinant molecule according to claim 4.

8. A nucleic acid sequence comprising a sequence encoding the peptide of claim 1 or a nucleic acid sequence which hybridizes under stringent hybridizing conditions to a nucleic acid sequence encoding the peptide of claim 1.

9. A transgenic plant comprising a foreign gene which encodes a peptide according to claim 1.

10. A method of combatting insect pests which comprises exposing said pests to an insecticidally effective amount of a peptide according to claim 1 wherein said peptide is expressed in a plant or plant colonizing microorganism as a result of genetic transformation.

11. An insecticidal composition comprising an insecticidally effective amount of a peptide according to claim 1 and an agriculturally acceptable carrier thereof.

12. An isolated protease inhibitor according to claim 1 wherein amino acid identity is at least 70%.

13. An isolated protease inhibitor according to claim 1 wherein amino acid identity is at least 90%.

14. An isolated protease inhibitor according to claim 1 wherein said inhibitor has the amino acid sequence extending from amino acid position 1 to 83 of SEQ ID NO.: 2.

15. The transgenic plant of claim 9 wherein said plant is maize.

16. The progeny of said maize plant of claim 15.

17. A method of combatting insect pests comprising exposing said pests to an insecticidally effective amount of a peptide according to claim 1.

18. The method of claim 17 wherein said insect pest is a Diabrotica sp.

19. A method of combatting insect pests comprising exposing said pests to an insecticidally effective amount of a peptide according to claim 13.

20. A host cell transformed with a vector according to claim 6.

21. The host cell of claim 20 wherein the cell is a maize, sweet corn, squash, melon, cucumber, sugarbeet, sunflower, rice, cotton, canola, sweet potato, bean, cowpea, soybean or alfalfa cell.

22. The method of claim 10 wherein said peptide is expressed in a plant colonizing microorganism as a result of genetic engineering.

* * * * *